United States Patent [19]

Li

[11] Patent Number: 4,590,011

[45] Date of Patent: May 20, 1986

[54] AMMOXIDATION PROCESS

[75] Inventor: Tao P. Li, Chesterfield, Mo.

[73] Assignee: Monsanto Company, St. Louis, Mo.

[21] Appl. No.: 742,000

[22] Filed: Jun. 6, 1985

Related U.S. Application Data

[63] Continuation of Ser. No. 554,502, Nov. 23, 1983, abandoned.

[51] Int. Cl.$^4$ .......................................... C07C 120/14
[52] U.S. Cl. ................................... 558/323; 502/249; 502/311
[58] Field of Search ...................................... 260/465.3

[56] References Cited

U.S. PATENT DOCUMENTS

| | | | |
|---|---|---|---|
| 3,164,626 | 1/1965 | Minekawa et al. | 260/465.3 |
| 3,242,847 | 9/1967 | Kruse | 260/465.3 |
| 3,335,169 | 8/1967 | Eden | 260/465.3 |
| 3,338,953 | 8/1967 | Malhotra | 260/465.3 |
| 3,446,834 | 5/1969 | Cavaterra et al. | 260/465.3 |
| 3,668,147 | 6/1972 | Yoshino et al. | 252/432 |
| 3,712,912 | 1/1973 | Hausweiler et al. | 260/465.3 |
| 3,882,159 | 5/1975 | Callahan et al. | 260/465.3 |
| 4,018,712 | 4/1977 | Li | 260/465.3 X |
| 4,052,450 | 10/1977 | Krabetz et al. | 260/465.3 X |
| 4,115,250 | 9/1978 | Flanders et al. | 208/120 |
| 4,151,117 | 4/1979 | Schlaefer | 260/465.3 X |
| 4,166,787 | 9/1979 | Blanton, Jr. et al. | 208/120 |
| 4,212,766 | 7/1980 | Brazdil et al. | 260/465.3 X |
| 4,252,632 | 2/1981 | Mooi | 208/120 |

*Primary Examiner*—Joseph Paul Brust
*Attorney, Agent, or Firm*—Thomas N. Wallin

[57] ABSTRACT

There is disclosed a process for the ammoxidation of hydrocarbons to unsaturated nitriles using a fluidized bed containing a mixture of active catalyst and discrete particles of an inert material to improve the yield of nitriles and inhibit the formation of by-products.

2 Claims, No Drawings

AMMOXIDATION PROCESS

This application is a continuation application of co-pending application Ser. No. 554,502 filed Nov. 23, 1983, now abandoned.

BACKGROUND OF THE INVENTION

1. Field of the Invention

The present invention relates to a process for the ammoxidation of light hydrocarbons, preferably olefins, to unsaturated nitriles, such as acrylonitrile.

2. Description of the Prior Art

It is well known that olefins can be oxidized to oxgenated hydrocarbons, such as unsaturated aldehydes and acids, for example acrolein and methacrolein, and acrylic and methacrylic acid. It is also well known that olefins can be ammoxidized to unsaturated nitriles such as acrylonitrile and methacrylonitrile. The value of these products is generally well recognized, with acrylonitrile being among the most valuable monomers available for producing useful polymeric products.

Many catalyst systems have been developed which are useful for oxidation and ammoxidation of light hydrocarbons, with special attention being given to the ammoxidation of propylene to form acrylonitrile.

One exceptionally active catalyst for oxidation/ammoxidation is the catalyst disclosed in my U.S. Pat. No. 4,018,712, the teachings of which are incorporated herein by reference. This catalyst contains the elements antimony, uranium, iron, bismuth, and molybdenum, and optionally, nickel or cobalt in a catalytically active oxidized state. This catalyst is exceptionally active and very suitable for the ammoxidation of propylene to acrylonitrile.

Other catalyst systems have been developed composed of oxides of molybdeum and tellurium, as described in U.S. Pat. No. 3,164,626, the teachings of which are incorporated herein by reference. A somewhat related catalyst for the ammoxidation of olefins composed of the oxides of tellurium and cerium is described in U.S. Pat. No. 3,446,834, the teachings of which are incorporated herein by reference.

It is also known to use in the ammoxidation process catalysts composed of oxides of molybdenum, tellurium, manganese, and phosphorus as described in U.S. Pat. No. 3,335,169, the teachings of which are incorporated herein by reference.

Another suitable catalyst for the ammoxidation process is composed of oxides of iron, antimony, vanadium, molybdenum, tungsten, and tellurium, as described in U.S. Pat. No. 3,668,147, the teachings of which are incorporated herein by reference.

Despite the great number of catalysts known to be useful for the oxidation/ammoxidation reactions, there is a continued need in the art to develop catalysts with even greater activity, and which increase the yield of desired products while minimizing yields of undesired products. In a relatively highly developed process, such as production of acrylonitrile by the ammoxidation of propylene, a very small yield increase, even on the order of ½ or 1%, represents a very significant commercial advance since the volume of acrylonitrile on a world-wide basis is extremely large.

It has been discovered that as catalyst activity increases, there are some attending undesirable consequences. The exact nature of the problem is difficult to fully understand based on present knowledge of what precisely occurs in the oxidation/ammoxidation process. It is believed that some undesirable gas phase reactions occur even in a well fluidized bed. This problem of side reactions seems to be worse with more active catalysts.

Another consequence of the use of more active catalysts is that as the activity of the catalyst has improved, the amount of feed and throughput increase, and heat generation due to the exothermic nature of the reactions, increases. Normally, plant facilities for making acrylonitrile cannot be extensively modified to but accommodate new and more active catalyst because of the large scale economies involved. Therefore, one must make do with the existing equipment with only minor modifications thereto. It is believed that the very enhanced activity of such catalysts, including the very active catalyst disclosed in the U.S. Pat. No. 4,018,712, referred to above presents a hindrance to optimum commercial operation in a process using such catalyst.

It has been discovered, quite unexpectedly, that addition of an inert material, such as alumina to dilute the catalyst significantly increases the yield of desired products, while minimizing in an acceptable manner the yield of undesirable by-products.

Accordingly, the present invention provides a process for oxidation/ammoxidation comprising charging to a fluidized bed oxidation/ammoxidation reaction zone containing a mixture of active oxidation/ammoxidation catalyst and particles of a relatively inert material having a particle size distribution compatible with fluidization in said reaction zone, and withdrawing from said reaction zone an oxidation/ammoxidation product.

In another embodiment, the present invention provides a process for the ammoxidation of propylene to acrylonitrile comprising charging to a fluidized bed ammoxidation reaction zone operated at ammoxidation conditions a feed comprising propylene, ammonia and oxygen, and wherein said ammoxidation reaction zone contains a fluidized bed mixture of active ammoxidation catalyst and particles of a relatively inert material having a particle size distribution compatible with fluidization in said ammoxidation reaction zone, and wherein acrylonitrile is withdrawn from said reaction zone as a produce of the process.

In a more specific embodiment, the present invention provides a process for the ammoxidation of propylene to acrylonitrile. The process involves feeding propylene, ammonia, and oxygen to a fluidized bed reaction zone. The resulting product, acrylonitrile, is recovered from the reaction zone. The fluidized bed in the reaction zone comprises a highly active ammoxidation catalyst comprised of antimony, uranium, and iron along with possibly other metals such as bismuth and molybdenum, preferably on a support. Where a support is used, the catalyst comprises at least 5% up to about 90%, preferably 10 to 50%, by weight of the catalytic composite material. Any known support materials can be used, such as, silica, alumina, zirconia, alundum, silicon carbide, aluminasilica, and the inorganic phosphates, silicates, aluminates, borates, and carbonates which are stable under the reaction conditions in the feed reaction zone and do not significantly reduce the catalytic activity of the active portion of the catalyst.

The composite catalyst is diluted with an inert substance which remains in the solid state in the reaction zone during the ammoxidation reaction. The resulting fluidized bed contains 2 to 50%, preferably 5 to 40% of the inert discrete particulate substances which has a particle size distribution compatible with fluidization. The inert substance can be silica, alumina, zirconia, alundum, silicon carbide, aluminasilica, and the inorganic phosphates, silicates, aluminates, borates, and carbonates which are stable under the reaction condition employed. Alpha-alumina is preferred. As a result, acrylonitrile in greater yields and by-products in lesser yields are produced as compared to the use of the same active ammoxidation catalyst not in association with inert discrete particles.

The preferred active ammoxidation catalyst has the following empirical formula $$Sb_aU_bFe_cBi_dMo_eMe_fO_g$$

Me is nickel or cobalt, a is 1–10, b is 0.1 to 5, c is 0.1 to 5, d is 0.001 to 0.1, e is 0.001 to 0.1, f is 0 to 0.1, and g is a number taken to satisfy the valences of the quantities of Sb, U, Fe, Bi, and Mo, including Ni and Co, if present, in the oxidation state in which they exist in the catalyst.

DETAILED DESCRIPTION

The catalyst which is suitable for use in the new process includes any super active ammoxidation catalyst where the addition of and association with a relatively inert material in a process for producing acrylonitrile from propylene, ammonia, and oxygen results in improved yields of acrylonitrile and reductions in the formation of by-products.

The preferred catalyst is disclosed in U.S. Pat. No. 4,018,712. However, the benefits obtained by practicing the invention may be observed with the use of other super active catalysts. If the catalyst is not very active, there probably is still some improvement due to the addition of fine inert particulate material. However, the improvement will not be as evident.

The inert material that is added in the process of my invention can be any particulate which does not interfere with the fluidizing properties of the catalyst used in the fluid bed, and which imparts no undesirable catalytic activity. Especially preferred is the use of low surface area alpha-alumina. The preferred physical properties of the alpha-alumina are set forth hereafter.

The catalyst can be prepared by any known method. Generally, one will use individual oxides or salts of the elements in the selected catalyst. One convenient method of preparing the catalyst is to first combine the oxides, sulfates, or the like if antimony, uranium, iron, and bismuth with sulfuric acid. When antimony sulfate is used as a starting material, it can be added to water wherein sulfuric acid is obtained. Nitric acid is used to oxidize the sulfate salts of the various elements or to further oxidize the oxides of the elements. Instead of using sulfuric acid to digest the metal oxides, nitric acid can be used. After the acid mixture has digested, the pH of the mixture is adjusted to the basic side to cause precipitation of the oxides. The precipitate is then filtered. After the filtering operation, the filter cake is dried at a suitable temperature of from about 100°–180° C. A catalyst support may be added prior to or subsequent to drying. A suitable drying temperature is about 110° C. However, drying can be obtained at higher temperatures such as up to about 650° C. The time over which drying is accomplished can range from an hour up to about 50 hours or more. Drying of the catalyst with or without the support can be advantageously accomplished, for example, by spray drying. The catalyst is calcined at a temperature in the range of about 500°–1150° C. The time of calcination can vary and depends upon the temperature employed. Generally, a time period of 1–24 hours at a selected temperature is sufficient. The calcination is preferred to be conducted in the presence of oxygen or air but may be conducted in the absence of oxygen, such as in a nitrogen atmosphere. The catalyst is shaped to suitable particle size having a desired surface area. The inert material also should have a desired size and surface area. It may be mixed with the catalyst before addition to the reaction zone. Also, the inert material and the catalyst can be added separately to the reaction zone. It is preferred that a composite of the inert particulate material and catalyst be formed so that the two components are randomly distributed and then moved together to the reaction zone. Preferably the catalyst has a surface area of about 10–100 m$^2$/g, a packing density of 0.9–1.1 g/ml, and an average particle size of 40–80 microns. The inert material has a surface area of less than 5m$^2$/g, preferably of about 0.5–3m$^2$/g, a packing density of 0.5 to 2 g/l but preferably in the range of 0.9–1.4 g/ml, and an average particle size of less than 150 microns, preferably of about 40–80 microns.

The catalyst diluted with the inert material exhibits exceptional utility in the conversion of olefins with or without the presence of ammonia. The olefins employed as reactants for the conversion by the catalyst of this invention may be open chain, as well as cyclic and include, for example, propylene, butene-1, butene-2, isobutene, pentene-1 pentene-2, 3-methyl butene-1, 2-methyl butene-2, hexene-1, hexene-2, 4-methyl pentene-1, 3,3-dimethylbutene-1, 4-methyl pentene-2, octene-1, cyclopentene, cyclohexene and the like. Particularly, when the diluted catalyst of the present invention is used as merely an oxidation catalyst, it is especially adapted to the conversion of propylene to acrolein and isobutylene to methacrolein. Of course, mixtures of olefins may be employed and mixtures of olefins with other hydrocarbons are applicable to the process of this invention. When the catalyst of the present invention is to be used as an ammoxidation catalyst, the olefins mentioned above are applicable. However, the modified catalyst of this invention is particularly adapted to the conversion of propylene with ammonia and oxygen to acrylonitrile at 250°–650° C.

The molar ratio of oxygen to the olefin in the feed will generally be in the range of 0.5:1 to 4:1 with a preferred ratio being 1:1 to 3:1. The molar ratio of ammonia to olefin in the feed will generally be in the range of 0.5:1 to 5:1 and preferably slightly over the stoichiometric ratio of 1:1 ammonia:olefin will be employed.

While ammonia is most generally employed as the nitrogen providing compound, other nitrogen containing materials may be employed which chemically change to produce reactive nitrogen under the selected reaction conditions. Any source of oxygen, pure or in admixture with inert gases, may be employed in the process of the invention. Air is a suitable source of oxygen.

As used in the examples below, the following terms have the following definitions:

% propylene (C$_3$H$_6$) Converted =

$$\frac{\text{mols C}_3\text{H}_6 \text{ in feed} - \text{mols C}_3\text{H}_6 \text{ in effluent}}{\text{mols C}_3\text{H}_6 \text{ in feed}} \times 10^0$$

$$\% \text{ product yield} = \frac{\text{mols C}_3\text{H}_6 \text{ converted to the product}}{\text{mols of C}_3\text{H}_6 \text{ in feed}} \times 100$$

"W/F" is defined as the weight of catalyst in grams divided by the flow rate of the reactor stream in ml/sec measured at STP.

EXAMPLE

The catalyst used in this example had a composition of $Sb_{1.85}U_{0.33}Fe_{0.66}Bi_{0.02}[Fe_2(MoO_4)_3]_{0.0133}$–45% $SiO_2$ and was prepared according to U.S. Pat. No. 4,018,712.
The catalyst has the following physical properties:
Surface Area: 66 m$^2$/g
Density, compact: 1.01 g/ml.
Particle size,: Less than 125 microns This super active catalyst was placed in a laboratory sized fluid bed reactor. The reactor internal diameter was 1.25 cm. There was added 25 grams of fresh catalyst to this reactor, for each test.

The inert material added to this reactor to test its effect on the process was 12.5 grams of alpha-alumina, Norton 81582, purchased from the Norton Company. This alumina had the following physical properties:
Surface Area: 0.18 m$^2$/g
Packed Density: 1.23 g/ml
Particle Size: Less than 125 microns All tests were conducted at 465° C., processing a feed with the following mole composition:
Propylene: 8.0%
Ammonia NH3: 8.4%
Oxygen: 17.5%
Helium: 66.1%

Commercially one would not normally operate a reactor with helium, but it is very convenient to do so in a laboratory for test purposes. Helium is relatively inert; and it is believed that the reaction conditions, yields, etc., roughly correspond to those that would be obtained in using air as an oxygen source.

The experiments were conducted at two pressures, roughly corresponding to relatively low and relatively high pressure commercial AN processes. The relatively low pressure was 13 psig, about 190,000 Pa. The relatively high pressure operation corresponds to 18 psig, or 225,000 Pa.

The resident times of reactants in the reactor, based upon the 25 grams of catalyst added, were held constant in all cases at 2.4 seconds. The feed rate necessarily changed to hold this contact time constant. The feed rate is reported as W/F as above defined.

The results are tabulated in the following Table.

TABLE

|  | LOW | LOW | HIGH | HIGH |
|---|---|---|---|---|
| Pressure, psig | 13 | 13 | 18 | 18 |
| Alumina dilution | no | yes | no | yes |
| W/F, g sec ml$^{-1}$ | 3.5 | 3.5 | 3 | 3 |
| Contact time, sec. | 2.4 |  | 2.4 |  |
| C$_3$H$_6$ Conv. % | 95.9 | 97.7 | 95.9 | 97.2 |
| Yield, % |  |  |  |  |
| AN | 76.3 | 77.4 | 74.5 | 75.6 |
| AcR | 0.8 | 0.3 | 0.4 | 0.3 |
| HCN | 5.9 | 6.0 | 6.1 | 6.2 |
| CO$_x$ | 12.6 | 13.9 | 14.5 | 14.6 |
| AcN | 0.2 | 0.2 | 0.3 | 0.5 |
| Carbon Balance, % | 99.0 | 98.5 | 98.9 | 98.3 |

In the above Table, AN refers to acrylonitrile, AcR refers to acrolein, HCN refers to hydrogen cyanide, CO$_x$ refers to CO$_2$ and CO, and AcN refers to acetonitrile.

These data show that the presence of a relatively inert diluent significantly increases the yield of acrylonitrile, by more than 1.0 weight % whether at a relatively low pressure operation or a relatively high pressure operation.

There is a reduction in the amount of acrolein production but the reduction is more apparent at low pressure than at high pressure.

The carbon balance was good for all tests. The carbon balance is calculated based on the moles of propylene fed to the reactor and the moles of products recovered by gas chromatographic analysis.

BEST MODE

If one were practicing this invention commercially today, one should add alumina, or other inert diluent to the reactors, limited only by the extra amount of material that the reactors could hold, and a possible maxima in desired product production. If the reactors were too small for a super active catalyst, one should remove some of the catalyst already present in the reactor to permit addition of more alumina.

Operation with a catalyst with alumina mixture containing from 2 to 50 weight % alumina will give satisfactory results, with best results obtained when the catalyst mixture contains 10 to 40 weight % diluent, preferably alumina.

It is possible, and frequently beneficial, to adjust the particle size distribution of the inert material to compliment the particle size distribution of the catalyst in the reactor. If the super active catalyst in the reactor is relatively deficient in small size particles, it would be best to use an inert diluent with a relatively high loading of small particles to improve bed fluidization characteristics. Alternatively, if the super active catalyst in the fluidized bed has an excessive amount of fines, the inert material could contain a particle size distribution skewed toward larger particles There also will be some benefit from having an inert diluent with a significantly different particle size distribution from that of the catalyst, the reason being that the inert diluent can be conveniently recovered and reused when some of the material in the reactor is purged and replaced with fresh catalyst to maintain overall catalyst activity.

I claim:

1. A process for the ammoxidation of propylene to acyrlonitirle comprising charging to a fluidized bed reaction zone a feed comprising propylene, ammonia, and oxygen and recovering from said reaction zone acrylonitrile as a product of the process, and wherein the reaction zone contains a fluidized bed of ammoxidation catalyst supported on SiO$_2$ and consisting essentially of the following formula $$Sb_aU_bFe_cBi_dMo_eMe_fO_g$$

wherein Me is Ni or Co, a is 1-10, b is 0.1 to 5, c is 0.1 to 5, d is 0.001 to 0.1, e is 0.001 to 0.1, f is 0 to 0.1, and g is a number taken to satisfy the valences of the quantities of Sb, U, Fe, Bi, and Mo, including Ni and Co, if present, and being physically mixed with an inert particulate material having a particle size distribution compatible with fluidization, said inert particulate material composing 2 to 50% by weight of the said bed and comprising alpha alumina with a surface area of less than 5m$^2$/g, a packing density of 0.9 to 1.4 g/ml and an average particle size less than about 150 microns.

2. Process of claim 1 wherein said catalyst has the composition of $Sb_{1.85}U_{0.33}Fe_{0.66}Bi_{0.02}[Fe_2(MoO_4)_3]_{0.0133}$–45% $SiO_2$.

* * * * *